United States Patent
Zhang et al.

(10) Patent No.: US 12,288,848 B2
(45) Date of Patent: Apr. 29, 2025

(54) IONIC LIQUID ELECTROLYTE FOR LITHIUM-ION BATTERIES

(71) Applicant: UCHICAGO ARGONNE, LLC, Chicago, IL (US)

(72) Inventors: Zhengcheng Zhang, Naperville, IL (US); Qian Liu, Darien, IL (US)

(73) Assignee: UCHICAGO ARGONNE, LLC, Chicago, IL (US)

( * ) Notice: Subject to any disclaimer, the term of this patent is extended or adjusted under 35 U.S.C. 154(b) by 0 days.

(21) Appl. No.: 18/240,938

(22) Filed: Aug. 31, 2023

(65) Prior Publication Data

US 2023/0420743 A1     Dec. 28, 2023

Related U.S. Application Data

(62) Division of application No. 16/722,413, filed on Dec. 20, 2019, now Pat. No. 11,784,350.

(51) Int. Cl.
| | |
|---|---|
| *H01M 10/0569* | (2010.01) |
| *C07D 207/06* | (2006.01) |
| *C07D 207/10* | (2006.01) |
| *C07D 211/14* | (2006.01) |
| *H01M 10/0525* | (2010.01) |

(52) U.S. Cl.
CPC ...... *H01M 10/0569* (2013.01); *C07D 207/06* (2013.01); *C07D 207/10* (2013.01); *C07D 211/14* (2013.01); *H01M 10/0525* (2013.01); *H01M 2300/0028* (2013.01)

(58) Field of Classification Search
CPC ..... H01M 10/0569; H01M 2300/0022; H01M 2300/0034; H01M 2300/0045; H01M 2300/0028
See application file for complete search history.

(56) References Cited

U.S. PATENT DOCUMENTS

| | | |
|---|---|---|
| 2011/0311884 A1 | 12/2011 | Armand et al. |
| 2012/0308882 A1 | 12/2012 | Ito et al. |

(Continued)

FOREIGN PATENT DOCUMENTS

| | | | |
|---|---|---|---|
| CN | 103387544 A | * | 11/2013 |
| CN | 103833675 A | * | 6/2014 |

(Continued)

OTHER PUBLICATIONS

S. Menne et al., "The synthesis and electrochemical characterization of bis(fluorosulfonyl)imide-based protic ionic liquids", Chemical Communications 51, 3656-3659 (Year: 2015).*

(Continued)

*Primary Examiner* — Ryan S Cannon
(74) *Attorney, Agent, or Firm* — OLSON & CEPURITIS, LTD.

(57) ABSTRACT

Described herein is a method of preparing an ionic liquid comprising a nitrogen or phosphorus cation and a bis(fluorosulfonyl)imidate (FSI) counter anion; the method comprising contacting a precursor selected from the group consisting of a tertiary amine, a tertiary phosphine, and an aromatic nitrogen heterocycle, with an alkyl bis(fluorosulfonyl)imidate in an aprotic solvent to alkylate the nitrogen or phosphorus of the precursor, and directly form a nitrogen or phosphorus cation with an FSI counter anion.

19 Claims, 5 Drawing Sheets

(56) References Cited

U.S. PATENT DOCUMENTS

| | | | |
|---|---|---|---|
| 2017/0077557 A1* | 3/2017 | Zheng | ............... H01M 10/0525 |
| 2020/0220223 A1 | 7/2020 | He et al. | |

FOREIGN PATENT DOCUMENTS

| | | |
|---|---|---|
| CN | 110093054 A | 8/2019 |
| JP | 2003257476 A | 9/2003 |
| JP | 2011124121 A | 12/2009 |

OTHER PUBLICATIONS

S. Menne, et al., "Supporting Information: Synthesis and electrochemical characterization of bis(fluorosulfonyl)imide-based protic ionic liquids" (Year: 2015).*

Machine translation of CN103387544A (Year: 2013).*

Machine translation of CN103833675A (Year: 2014).*

Endres, F., Ionic Liquids: Promising Solvents for Electrochemistry, Z. Phys. Chem. 218, 255-283 (2004).

Hagiwara, R. et al., Room Temperature Ionic Liquids of Alkylimidazolium Cations and Fluoroanions, Journal of Fluorine Chemistry 105, 221-227 (2000).

Hallett, J.P. et al., Room-Temperature Ionic Liquids: Solvents for Synthesis and Catalysis.2, Chemical Review 111, 3508-3576 (2011).

Jow, T.R. et al., (Eds), Abe, K., Nonaqueous Electrolytes and Advances in Additives, Electrolytes for Lithium and Lithium-Ion Batteries, Springer, Chapter 3, 167-182 (2014).

Jow, T.R. et al., (Eds), Matsumoto, H.., Recent Advances in Ionic for Lithium Secondary Batteries, Modern Aspects of Electrochemistry 58: Electrolytes for Lithium and Lithium-Ion Batteries, Springer, Chapter 4, 209-225 (2014).

Rogers, R.D. et al.. Ionic Liquids—Solvents of the Future?, Science 302, 5646, 792-793 (2003).

Wasserscheid, P. et al., Ionic Liquids in Synthesis, vol. 1 (Eds): Trulove, P.C. et al., Electrochemical Properties of Ionic Liquids, 141-170 (2003).

Bouvet, C.B. et al., Chiral and Redox-Active Room-Temperature Ionic Liquids Based on Ferrocene and L-Proline, European Journal Inorganic Chemistry, 4573-4580 (2016).

Hawker, R.R. et al., Variation of the Cation of Ionic Liquids: The Effects on Their Physiochemical Properties and Reaction Outcome, University of New South Wales, School of Chemistry, 0. A. Attanasi, D. Spinelli (ed.) Targets in Heterocyclic Systems: Chemistry and Properties vol. 18, SOC Chimica Italiana, p. 141-213 (2015).

Jannasch, P. et al., "Charge Transport in Nonstoichiometric 2-fluoropyridinium Triflate Protic Ionic Liquids", Journal of Physical Chemistry C 123, p. 23427-23432 (Year: 2019).

Nairoukh, Z. et al., "The Formation of All-Cis-(multi)fluorinated Piperidines by a Dearomatization-Hydrogenation Process", Nature Chemistry 11, p. 264-270 (2019).

Le, M.P et al., "Electrolyte Based on Fluorinated Cyclic Quaternary Ammonium Ionic Liquids", Ionics 18, p. 817-827 (2012).

* cited by examiner

IONIC LIQUID ELECTROLYTE FOR LITHIUM-ION BATTERIES

CROSS-REFERENCE TO RELATED APPLICATIONS

This application is a divisional of U.S. Ser. No. 16/722,413 filed on Dec. 20, 2019, which is incorporated herein by reference in its entirety.

STATEMENT OF GOVERNMENT INTEREST

The United States Government has rights in this invention pursuant to Contract No. DE-AC02-06CH11357 between the United States Government and UChicago Argonne, LLC representing Argonne National Laboratory.

FIELD OF THE INVENTION

This invention relates to electrolyte materials for use in lithium electrochemical cells and batteries. More particularly, this invention relates to an ionic liquid useful as an electrolyte for lithium ion batteries.

BACKGROUND

The lithium-ion battery (LIB) has been widely used in daily modern life. There is a strong need for next generation LIBs with high energy density and cycling performance, particularly for electric vehicle applications. To increase the energy density of conventional LIB, popular approaches are to elevate the operational potential of the cathode or the voltage of the cell. However, at high potentials or high voltages, the state-of-the-art (SOA) organic carbonate solvent-based electrolytes tend to be oxidatively decomposed at the cathode surface causing gassing, low Coulombic efficiency, transition metal ion dissolution, and rapid capacity fade of the full cell. Moreover, these conventional electrolytes are extremely flammable due to their high vapor pressure and low flashpoint, which leads to potential safety issues especially when applied in electric vehicles. Another widely explored approach for enhancing the energy density is to incorporate high specific capacity electrodes to the LIB, such as Li-air, Li—S, Si anodes and Li-metal anodes. While Li metal has a high specific capacity (3860 mAh/g) and the lowest redox potential, the development of Li metal anodes has been hindered due to safety issues related to lithium dendrite formation and the high reactivity of lithium with the SOA organic carbonate electrolyte solvents.

To address these electrolyte related issues, room-temperature ionic liquids (ILs) have been explored as potential alternatives for conventional carbonate electrolytes, and have attracted a lot of interest due to their intrinsic physical properties, such as low vapor pressure, relative non-flammability, wide electrochemical window and high ionic conductivity. However, these ion-liquid electrolyte systems often suffer from high viscosity, poor wettability and poor SEI formation issue, which have limited their applications in commercial LIBs. ILs based on bis(fluorosulfonyl)imide (FSI) anion have shown superior performance compared to the bis(trifluoromethylsulfonyl)imide (TFSI) analogues, due to their relatively lower viscosity, higher conductivity and capability of forming stable SEI layer on graphite anode.

Previous studies of ILs were mainly focused on low Li salt concentration (<1 M) in order to avoid the high viscosity of ILs with higher lithium concentrations. A super-concentrated 1-methyl-1-propylpiperidinium bis(fluorosulfonyl) imide (PMpipFSI) electrolyte has been developed at Argonne National Laboratory, which enables stable cycling in a $LiNi_{0.5}Mn_{0.3}Co_{0.2}O_2$ oxide-lithium (NMC532/Li) cell up to 4.7 V. While this electrolyte system shows promise, there still is a need for alternative ionic liquids with improved viscosity and good SEI formation, among other properties.

There is an ongoing need for new IL electrolytes in lithium-ion batteries with desirable properties such as high lithium content, good SEI formation, and low viscosity. The ionic liquid electrolytes described herein address this need.

SUMMARY

The ionic liquids disclosed herein are salts comprising a nitrogen or phosphorus such as a quaternary ammonium ion, a quaternary phosphonium ion, or an N-alkylated nitrogen heterocycle, and which include at least one functional substituent, e.g., a fluoro, cyano, carbonate ester, alkenyl group, or alkynyl group bonded to a carbon atom the cation. In a preferred embodiment, the cation is represented by the structure of Formula (I):

wherein $Z^1$ is N or P; x is 0 or 1; each of $R^1$ and $R^2$ independently comprises a hydrocarbyl group (e.g., alkyl, aryl, aryl-substituted alkyl, alkyl-substituted aryl, and the like), or $R^1$ and $R^2$ together with $Z^1$ constitute an aromatic or non-aromatic heterocyclic ring. When $R^1$ and $R^2$ together with $Z^1$ constitute an aromatic heterocyclic ring, x is 0, and $Z^1$ is N. When $R^1$ and $R^2$ together with $Z^1$ constitute a non-aromatic heterocyclic ring, x is 1. Each of $R^3$ and $R^4$ independently comprises a hydrocarbyl group. One or more of the hydrocarbyl groups, the aromatic heterocyclic ring, and the non-aromatic heterocyclic ring of the cation bears at least one substituent comprising a fluoro, cyano, carbonate ester, alkenyl group (e.g., allyl or vinyl), or alkynyl group (e.g., propargyl).

Non-limiting examples of hydrocarbyl groups include, for example, an alkyl group, an aryl group (e.g., phenyl or alkyl-substituted phenyl), or an aryl-substituted alkyl group (e.g., benzyl or 2-phenylethyl).

When $R^1$ and $R^2$ together with $Z^1$ form a heterocyclic ring, the ring can be aromatic or non-aromatic. Aromatic heterocyclic rings include aromatic 5-membered heterocyclic rings such as, e.g., an imidazole, a 1,3-thiazole, and a 1,3-oxazole and the like; and aromatic 6-membered heterocyclic rings such as, e.g., a pyridine, a 1,4-pyrazine, a 1,3-pyrazine, a 1,3,5-triazine, a 1,2,4-triazine, or a 1,2,3-triazine and the like. Non-aromatic heterocyclic rings include, for example, non-aromatic 5-membered heterocyclic rings (e.g., a pyrrolidine, a −3-pyrrolidone, and the like); and non-aromatic 6-membered heterocyclic ring (e.g., a piperidine, a piperrazine, a morpholine, and the like).

In some embodiments, the cation comprises a quaternary ammonium or quaternary phosphonium cation with four pendent hydrocarbyl groups ($R^1$, $R^2$, $R^3$ and $R^4$), at least one of which bears the at least one substituent selected from the group consisting of fluoro, cyano, and alkenyl (e.g., allyl).

The hydrocarbyl groups preferably are alkyl, aryl or a combination of alkyl and aryl (e.g., benzyl and the like).

In some embodiments $R^1$ and $R^2$ together with $Z^1$ constitute a heterocyclic ring and the cation has a formula selected from the groups consisting of Formula (II), (III), (IV) and (V).

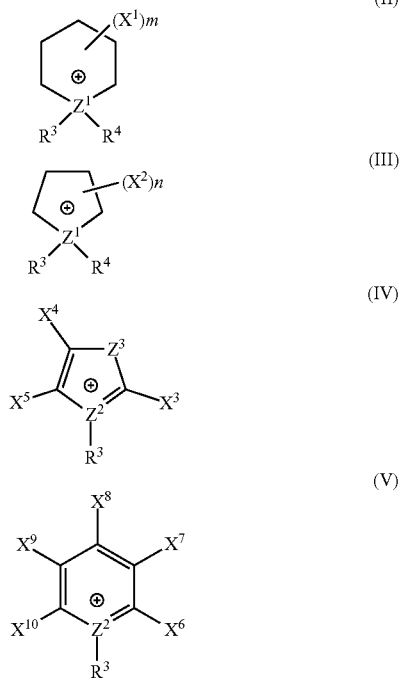

The cations of Formula (II), (III), (IV) and (V) are non-limiting examples of cations of Formula (I) in which $R^1$ and $R^2$ together with $Z^1$ constitute a non-aromatic 6-membered heterocyclic piperidine ring (Formula (II)), a non-aromatic 5-membered heterocyclic pyrrolidine ring (Formula (III)), an aromatic 5-membered heterocyclic ring (Formula (IV)), and an aromatic 6-membered heterocyclic pyridine ring (Formula (V)).

In Formula (II), $Z^1$ is N or P, each $X^1$ independently is H, F, CN, carbonate ester, alkenyl, alkynyl, fluoro-substituted alkyl, or cyano-substituted alkyl; n is 0 or an integer from 1 to 10; and $R^3$ and $R^4$ are as defined in Formula (I), and at least one of $X^1$, $R^3$, and $R^4$ bears at least one substituent comprising a fluoro, cyano, carbonate ester, alkenyl group (e.g., allyl or vinyl), or alkynyl group (e.g., propargyl).

In Formula (III), $Z^1$ is N or P, each $X^2$ independently is H, F, CN, alkenyl, alkynyl, fluoro-substituted alkyl, or cyano-substituted alkyl; n is 0 or an integer from 1 to 8; and $R^3$ and $R^4$ are as defined in Formula (I), and at least one of $X^2$, $R^3$, and $R^4$ bears at least one substituent comprising a fluoro, cyano, carbonate ester, alkenyl group (e.g., allyl or vinyl), or alkynyl group (e.g., propargyl).

In Formula (IV), $Z^2$ is N; $Z^3$ is N, O, or S; each of $X^3$, $X^4$, and $X^5$ independently is H, alkyl, F, CN, alkenyl, alkynyl, fluoro-substituted alkyl, or cyano-substituted alkyl; and $R^3$ is as defined in Formula (I), and at least one of $X^3$, $X^4$, $X^5$, and $R^3$ bears at least one substituent comprising a fluoro, cyano, carbonate ester, alkenyl group (e.g., allyl or vinyl), or alkynyl group (e.g., propargyl).

In Formula (V), $Z^2$ is N; each of $X^6$, $X^7$, $X^8$, $X^9$, and $X^{10}$ independently is H, alkyl, F, CN, alkenyl, alkynyl, fluoro-substituted alkyl, or cyano-substituted alkyl; and $R^3$ is as defined in Formula (I), and at least one of $X^6$, $X^7$, $X^8$, $X^9$, $X^{10}$, and $R^3$ bears at least one substituent comprising a fluoro, cyano, carbonate ester, alkenyl group (e.g., allyl or vinyl), or alkynyl group (e.g., propargyl).

The anion of the ionic liquid can be can be any anion that will provide an ionic liquid salt, such as, e.g., fluoroborate anion such as tetrafluoroborate ($BF_4^-$), pentafluorethyl-trifluoroborate ($CF_3CH_2BF_3^-$), and the like; fluorinated bis-sulfonamides such as $N(SO_2F)_2^-$ (FSI), $N(SO_2CF_3)_2^-$ (TFSI), and the like; fluorinated diazolide anions such as 1-trifluoromethyl-3-cyano-4-cyano imidazolide anion (TDI), 3,5-trifluoromethyl-1,2-diazolide anion (TFPI), and the like.

A method of preparing FSI salts of nitrogen and phosphorus cations, such as, e.g., ionic liquids of Formula (I) also is described herein.

Ionic liquids comprising alkenyl-substituted cations of Formula (II), such as N-methyl-N-allylpyrrolidium cation can provide lower viscosity that the corresponding saturated materials, and can participate in solid electrolyte interface (SEI) formation, e.g., by polymerization of the allyl group on the graphite surface. Ionic liquids comprising fluoro-substituted cations of Formula (II), such as N-methyl-N-propyl-3-fluoropyrrolidium cation, N-methyl-N-propyl-3,4-difluoropyrrolidium cation, and N-methyl-N-3,3,3,2,2-pentafluoropropylpyrrolidium cation can provide high voltage stability, SEI formation, and suppress flammability. Additionally, ionic liquids comprising N-methyl-N-3-cyanopropyl-pyrrolidium cation or N-methyl-N-propyl-3,4-cyclocarbonatopyrrolidium cation can provide voltage stability, solid electrolyte interface (SEI) formation, and cathode electrolyte interface (CEI) formation, both of which can passivate the electrode surfaces and ameliorate electrolyte decomposition at the electrode surfaces.

The following non-limiting examples of embodiments of the electrolytes and materials described herein are provided to illustrate certain features and expects of the present invention.

Embodiment 1 is an ionic liquid comprising a cation of Formula (I) and a counter anion:

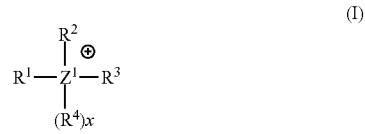

wherein:
$Z^1$ is N or P;
x is 0 or 1;
each of $R^1$ and $R^2$ independently comprises a hydrocarbyl group, or $R^1$ and $R^2$ together with $Z^1$ constitute an aromatic or non-aromatic heterocyclic ring;
when $R^1$ and $R^2$ together with $Z^1$ constitute an aromatic heterocyclic ring, x is 0, and $Z^1$ is N;
when $R^1$ and $R^2$ together with $Z^1$ constitute a non-aromatic heterocyclic ring, x is 1;
each of $R^3$ and $R^4$ independently comprises an a hydrocarbyl group; and
one or more of the hydrocarbyl groups, the aromatic heterocyclic ring, and the non-aromatic heterocyclic ring bears at least one substituent comprising a fluoro, cyano, a carbonate ester, alkenyl group, or alkynyl group.

Embodiment 2 is the ionic liquid of embodiment 1, wherein $R^1$ and $R^2$ together with $Z^1$ constitute a heterocyclic ring selected from the group consisting of an aromatic 5-membered heterocyclic ring and an aromatic 6-membered heterocyclic ring.

Embodiment 3 is the ionic liquid of embodiment 2, wherein the aromatic 5-membered heterocyclic ring is selected from the group consisting of an imidazole, a 1,3-thiazole, and a 1,3-oxazole; and the aromatic 6-membered heterocyclic ring is selected from the group consisting of a pyridine, a 1,4-pyrazine, a 1,3-pyrazine, a 1,3,5-triazine, a 1,2,4-triazine, and a 1,2,3-triazine.

Embodiment 4 is the ionic liquid of any one of embodiments 2 and 3, wherein one or more carbon of the aromatic 5-membered heterocyclic ring and one or more carbon of the aromatic 6-membered heterocyclic ring bears the at least one substituent selected from the group consisting of fluoro, cyano, alkenyl, alkynyl, a carbonate ester, fluoro-substituted alkyl, or cyano-substituted alkyl.

Embodiment 5 is the ionic liquid of any one of embodiments 1 to 4, wherein $R^1$ and $R^2$ together with $Z^1$ constitute a heterocyclic ring selected from the group consisting of a non-aromatic 5-membered heterocyclic ring and a non-aromatic 6-membered heterocyclic ring.

Embodiment 6 is the ionic liquid of embodiment 5, wherein the non-aromatic 5-membered heterocyclic ring is selected from the group consisting of a pyrrolidine and a 3-pyrrolidone; and the non-aromatic 6-membered heterocyclic ring is selected from the group consisting of a piperidine, a piperrazine, and a morpholine.

Embodiment 7 is the ionic liquid of any one of embodiments 5 and 6, wherein one or more carbon of the non-aromatic 5-membered heterocyclic ring and one or more carbon of the non-aromatic 6-membered heterocyclic ring bears the at least one substituent selected from the group consisting of fluoro, cyano, alkenyl, alkynyl, a carbonate ester, fluoro-substituted alkyl, or cyano-substituted alkyl.

Embodiment 8 is the ionic liquid of embodiment 7, wherein n is 1, each of $R^1$, $R^2$, $R^3$ and $R^4$ independently is an alkyl group, and at least one of $R^1$, $R^2$, $R^3$ and $R^4$ bears the at least one substituent selected from the group consisting of fluoro, cyano, alkenyl, alkynyl, or a carbonate ester.

Embodiment 9 is the ionic liquid of embodiment 8, wherein the alkyl group is a $C_1$ to $C_6$ alkyl group.

Embodiment 10 is the ionic liquid of any one of embodiments 1 to 9, wherein the anion of the ionic liquid is selected from the group consisting of a fluoroborate anion, a fluorinated bis-sulfonamide anion, and a fluorinated diazolide anion.

Embodiment 11 is the ionic liquid of embodiment 10, wherein:
(a) the fluoroborate anion is selected from the group consisting of tetrafluoroborate ($BF_4^-$) and pentafluoroethyl-trifluoroborate ($CF_3CH_2BF_3^-$);
(b) the fluorinated bis-sulfonamide anion is selected from the group consisting of $N(SO_2F)_2^-$ and $N(SO_2CF_3)_2^-$; and
(c) the fluorinated diazolide anion is selected from the group consisting of 1-trifluoromethyl-3-cyano-4-cyano imidazolide anion and 3,5-trifluoromethyl-1,2-diazolide anion.

Embodiment 12 is an ionic liquid comprising a nitrogen or phosphorous cation and a counter anion, wherein the cation ion has a formula selected from the groups consisting of Formula (II), (III), (IV) and (V):

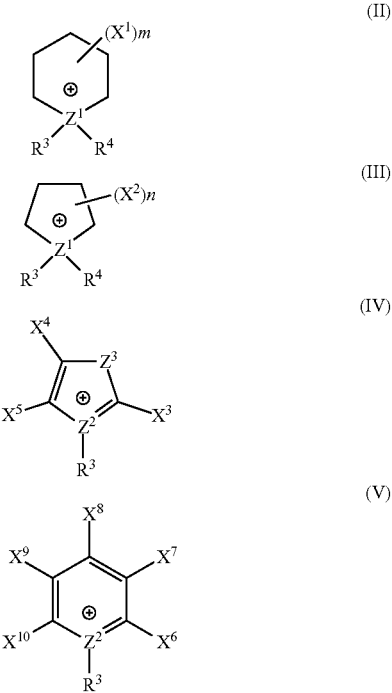

wherein:
$Z^1$ is N or P;
$Z^2$ is N;
m is 0 or an integer from 1 to 10;
n is 0 or an integer from 1 to 8;
each $X^1$ and $X^2$ independently is F, CN, alkenyl, alkynyl, a carbonate ester, fluoro-substituted alkyl, or cyano-substituted alkyl;
each $X^3$, $X^4$, $X^5$, $X^6$, $X^7$, $X^8$, $X^9$, and $X^{10}$ independently is H, alkyl, F, CN, alkenyl, fluoro-substituted alkyl, or cyano-substituted alkyl;
each of $R^3$ and $R^4$ independently comprises an a hydrocarbyl group; and
one or more of $R^3$, $R^4$, $X^1$, $X^2$, $X^3$, $X^4$, $X^5$, $X^6$, $X^7$, $X^8$, $X^9$, and $X^{10}$ bears at least one substituent comprising a fluoro, cyano, carbonate ester, alkenyl group, or alkynyl group Embodiment 13 is the ionic liquid of embodiment 12, wherein the anion of the ionic liquid is selected from the group consisting of a fluoroborate anion, a fluorinated bis-sulfonamide anion, and a fluorinated diazolide anion.

Embodiment 14 is the ionic liquid of embodiment 13, wherein:
(a) the fluoroborate anion is selected from the group consisting of tetrafluoroborate ($BF_4^-$) and pentafluoroethyl-trifluoroborate ($CF_3CH_2BF_3^-$);
(b) the fluorinated bis-sulfonamide anion is selected from the group consisting of $N(SO_2F)_2^-$ and $N(SO_2CF_3)_2^-$; and
(c) the fluorinated diazolide anion is selected from the group consisting of 1-trifluoromethyl-3-cyano-4-cyano imidazolide anion and 3,5-trifluoromethyl-1,2-diazolide anion.

Embodiment 15 is an electrolyte for a lithium ion battery comprising a lithium salt dissolved in the ionic liquid of any one of embodiments 1 to 14.

Embodiment 16 is the electrolyte of embodiment 15, wherein the lithium salt is selected from the group consisting of lithium bis(trifluoromethanesulfonyl)imide, lithium 2-trifluoromethyl-4,5-dicyanoimidazolate, lithium 4,5-dicyano-1,2,3-triazolate, lithium trifluoromethanesulfonate, lithium perchlorate, lithium bis(oxalato)borate, lithium difluoro(oxalato)borate, lithium tetrafluoroborate, lithium hexafluorophosphate, lithium thiocyanate, lithium bis(fluorosulfonyl)imidate, lithium bis(pentafluoroethylsulfonyl)imidate, lithium tetracyanoborate, lithium nitrate, and a combination of two or more thereof.

Embodiment 17 is the electrolyte of any one of embodiments 15 and 16, wherein the lithium salt is present at a concentration in the range of about 1 molar (M) to about 5 M.

Embodiment 18 is an electrochemical cell comprising an anode, a cathode, and an electrolyte comprising a lithium salt dissolved in the ionic liquid of any one of embodiments 1 to 14 contacting the anode, the cathode.

Embodiment 19 is the electrochemical cell of embodiment 18, wherein the lithium salt is present in the ionic liquid at a concentration in the range of 1 M to about 5 M.

Embodiment 20 is a battery comprising a plurality of electrochemical cells of any one of embodiments 18 and 19 electrically connected together in series, in parallel, or in both series and parallel.

Embodiment 21 is a method of preparing an ionic liquid comprising a nitrogen or phosphorus cation and a bis(fluorosulfonyl)imidate (FSI) counter anion; the method comprising contacting a precursor selected from the group consisting of a tertiary amine, a tertiary phosphine, and an aromatic nitrogen heterocycle, with an alkyl bis(fluorosulfonyl)imidate in an aprotic solvent to alkylate the nitrogen or phosphorus of the precursor, and directly form a nitrogen or phosphorus cation with an FSI counter anion.

BRIEF DESCRIPTION OF THE DRAWINGS

The invention consists of certain novel features and a combination of parts hereinafter fully described, illustrated in the accompanying drawings, it being understood that various changes in the details may be made without departing from the spirit, or sacrificing any of the advantages of the present invention.

DETAILED DESCRIPTION OF SELECTED EMBODIMENTS

Figure 1:
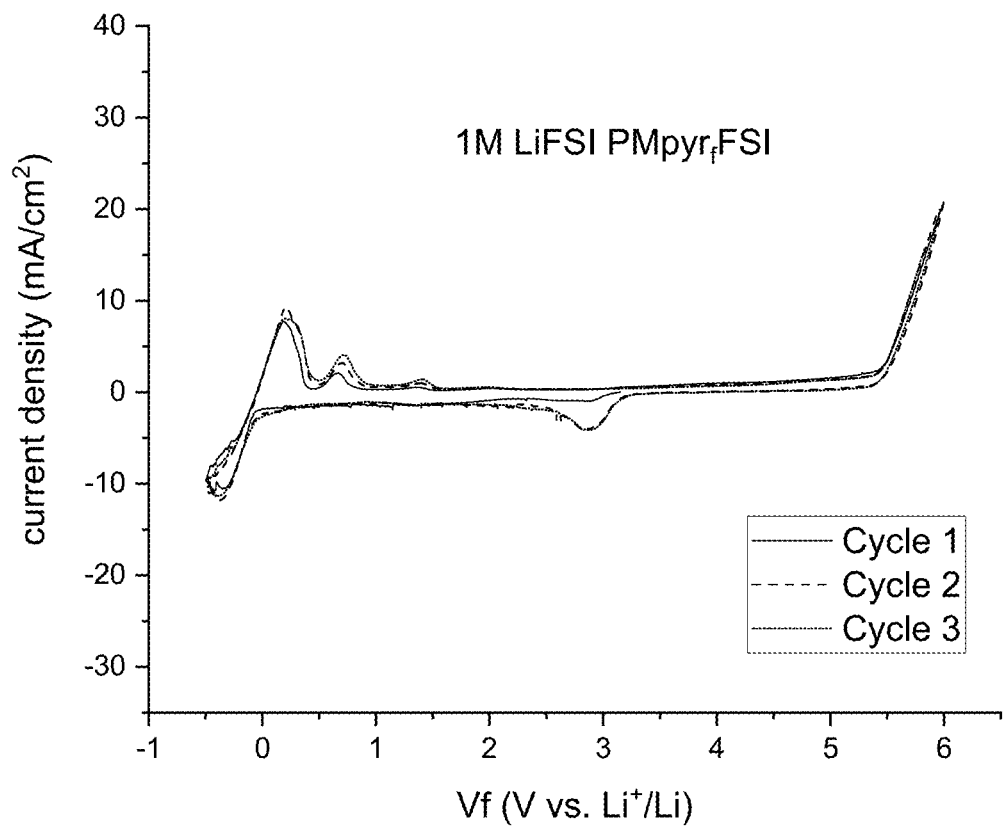
FIG. 1 shows a cyclic voltammetry plot of PMpyr$_f$FSI with 1 M LiFSI.

Ionic liquids comprising cations of Formula (I) that include functional substituents such as fluoro, cyano, and/or alkenyl substituents, provide a number of advantages over similar materials that lack the functional substituents. For examples, ionic liquids comprising the alkenyl, alkynyl, fluoro, cyano and carbonate groups can participate in SEI formation at the anode, which is lacking from prior art ionic liquids. The alkenyl group also lowers viscosity relative to ionic liquids with a similar, but non-functionalized cation. The fluoro substituents can also provide some flame retardant properties especially substituents with several fluoro groups, such as perfluoroethyl, 3,3,3,2,2-pentafluoro propyl, and the like. In addition, cyano and carbonate groups can participate in CEI formation.

In Formula (I):

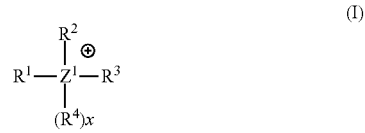

$Z^1$ is N or P;

x is 0 or 1;

each of $R^1$ and $R^2$ independently comprises a hydrocarbyl group, or $R^1$ and $R^2$ together with $Z^1$ constitute an aromatic or non-aromatic heterocyclic ring;

when $R^1$ and $R^2$ together with $Z^1$ constitute an aromatic heterocyclic ring, x is 0, and $Z^1$ is N;

when $R^1$ and $R^2$ together with $Z^1$ constitute a non-aromatic heterocyclic ring, x is 1;

each of $R^3$ and $R^4$ independently comprises an hydrocarbyl group; and one or more of the hydrocarbyl groups, the aromatic heterocyclic ring, and the non-aromatic heterocyclic ring bears at least one substituent comprising a fluoro, cyano, carbonate ester, alkenyl group, or alkynyl group.

As used herein, the term "ionic liquid" refers to a materials made up only from ions (i.e., salts) and are liquids at temperatures below about 100° C. Preferred ionic liquids are in a liquid state at ambient room temperature (e.g., about 20 to 25° C.).

The terms "hydrocarbon" and "hydrocarbyl" as used herein describe organic compounds or groups consisting exclusively of the elements carbon and hydrogen. These moieties include alkyl, alkenyl, alkynyl, aryl, carbocyclic moieties, and any combination of two or more thereof. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 30 total carbon atoms.

The term "alkyl" as used herein denotes saturated hydrocarbon moieties. Preferably, an alkyl group comprises 1 to 20 carbon atoms in the principal chain (e.g., 1 to 12 carbon atoms) and e.g., up to 30 total carbon atoms. These moieties may be straight or branched chain and include methyl, ethyl, propyl, isopropyl, butyl, hexyl, octyl, and similar groups.

The term "alkenyl" as used herein denotes a univalent hydrocarbon group containing a double bond. Preferably, alkenyl groups comprise 2 to 20 carbon atoms (e.g., 2 to 12 carbon atoms) in the principal chain, and up to 30 total carbon atoms. The alkenyl groups may be straight or branched chain, or cyclic, and include ethenyl (vinyl), propenyl, isopropenyl, butenyl, isobutenyl, hexenyl, octenyl, oleyl, and the like.

The term "alkynyl" as used herein denotes a univalent hydrocarbon group containing a carbon-carbon triple bond. Preferably, alkynyl groups comprise 2 to 20 carbon atoms (e.g., 2 to 12 carbon atoms) in the principal chain, and up to 30 total carbon atoms. The alkynyl groups may be straight or branched chain, and include ethynyl, propynyl (also referred to as propargyl), butynyl, isobutynyl, hexynyl, octynyl, and the like.

The term "aromatic" as used herein denotes chemical compounds or groups that contain conjugated planar ring systems with delocalized pi electron clouds instead of discrete alternating single and double bonds. The term "aromatic" encompasses the "aryl" and "heteroaryl" groups defined below.

The terms "aryl" or "Ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, anthracenyl, substituted phenyl, substituted biphenyl or substituted naphthyl.

The term "heteroaryl" as used herein alone or as part of another group denote optionally substituted aromatic groups having at least one heteroatom in at least one ring, and preferably 5 or 6 atoms in each ring. The heteroaryl group preferably has 1 or 2 oxygen atoms and/or 1 to 4 nitrogen atoms in the ring, and is bonded to the remainder of the molecule through a carbon. Exemplary heteroaryls include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl and the like.

As used herein, the term "quaternary ammonium" refers to a cation with a positively charged (+1) nitrogen atom and four hydrocarbyl groups covalently bonded to the nitrogen atom. Similarly, as used herein, the term "quaternary phosphonium" refers to a cation with a positively charged (+1) phosphorus atom and four hydrocarbyl groups covalently bonded to the phosphorus atom.

A "substituted" group, as described herein (e.g., substituted hydrocarbyl, alkyl, heteroaryl, aryl and heterocyclic moieties) is a group in which one or more hydrogen of the hydrocarbyl, alkyl, heteroaryl, aryl or heterocyclic group is replace by a specified substituent, such as a fluoro group, a cyano group, an alkenyl group, or a carbonate group.

For example, in some embodiments one or more of the hydrocarbyl groups comprising at least one alkenyl substituent can be, e.g., vinyl, allyl, propenyl, and the like; one or more of the hydrocarbyl groups comprising at least one alkynyl substituent can be, e.g., a terminal alkyne such as propargyl, or an internal alkyne such as 2-butynyl, and the like; one or more of the hydrocarbyl groups comprising at least one fluoro substituent can be, e.g., monofluoroalkyl, difluoroalkyl, trifluoroalkyl (trifluoromethyl, 2,2,2-trifluoroethyl, and the like), perfluoroalkyl (e.g., trifluoromethyl, pentafluoroethyl; heptafluoropropyl, and the like); one or more of the hydrocarbyl groups comprising at least one cyano substituent can be, e.g., cyanomethyl, 2-cyanoethyl, 3-cyanopropyl, and the like; and one or more of the hydrocarbyl groups comprising at least one carbonate ester substituent can be, e.g., an alkyl group (e.g., a $C_1$ to $C_6$ alkyl) bearing a methyl carbonate group (—OC(=O)OCH$_3$), an ethyl carbonate (—OC(=O)OCH$_2$CH$_3$), a cyclic carbonate on two adjacent carbons of the alkyl group; and the like.

In some embodiments, $R^1$ and $R^2$ together with $Z^1$ constitute an aromatic 5-membered heterocyclic ring (e.g., an imidazole, a 1,3-thiazole, and a 1,3-oxazole and the like). Optionally, one or more carbon of the aromatic 5-membered heterocyclic ring can bear the at least one substituent selected from the group consisting of fluoro, cyano, alkenyl, alkynyl, fluoro-substituted alkyl, or cyano-substituted alkyl.

In some other embodiments, $R^1$ and $R^2$ together with $Z^1$ constitute an aromatic 6-membered heterocyclic ring (e.g., a pyridine, a 1,4-pyrazine, a 1,3-pyrazine, a 1,3,5-triazine, a 1,2,4-triazine, or a 1,2,3-triazine and the like). Optionally, one or more carbon of the aromatic 6-membered heterocyclic ring can bear the at least one substituent selected from the group consisting of fluoro, cyano, alkenyl, alkynyl, fluoro-substituted alkyl, or cyano-substituted alkyl.

In some embodiments, $R^1$ and $R^2$ together with $Z^1$ constitute a non-aromatic 5-membered heterocyclic ring (e.g., a pyrrolidine, a –3-pyrrolidone, and the like). Optionally, one or more carbon of the non-aromatic 5-membered heterocyclic ring can bear the at least one substituent selected from the group consisting of fluoro, cyano, alkenyl, alkynyl, fluoro-substituted alkyl, or cyano-substituted alkyl. In some other embodiments, $R^1$ and $R^2$ together with $Z^1$ constitute a non-aromatic 6-membered heterocyclic ring (e.g., a piperidine, a piperrazine, a morpholine, and the like). Optionally, one or more carbon of the non-aromatic 6-membered heterocyclic ring can bear the at least one substituent selected from the group consisting of fluoro, cyano, alkenyl, alkynyl, fluoro-substituted alkyl, or cyano-substituted alkyl.

In some embodiments, the cation comprises a quaternary ammonium or quaternary phosphonium cation with four pendent alkyl groups ($R^1$, $R^2$, $R^3$ and $R^4$), at least one of which bears the at least one substituent selected from the group consisting of fluoro, cyano, alkenyl (e.g., allyl) and alkynyl (e.g., propargyl).

In some embodiments $R^1$ and $R^2$ together with $Z^1$ constitute a heterocyclic ring and the cation has a formula selected from the groups consisting of Formula (II), (III), (IV) and (V). (X)m

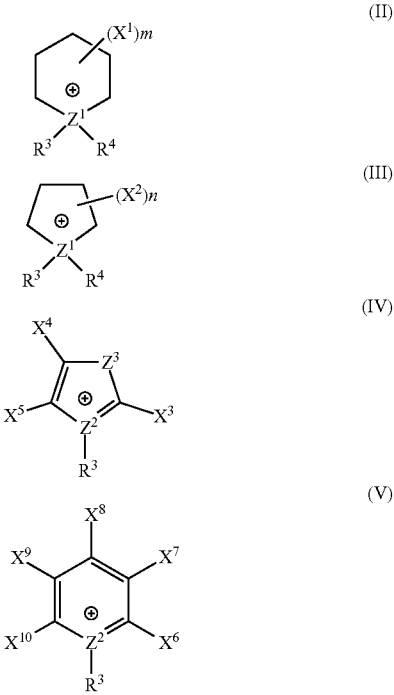

The cations of Formula (II), (III), (IV) and (V) are non-limiting examples of cations of Formula (I) in which $R^1$ and $R^2$ together with $Z^1$ constitute a non-aromatic 6-membered heterocyclic piperidine ring (Formula (II)), a non-aromatic 5-membered heterocyclic pyrrolidine ring (Formula (III)), an aromatic 5-membered heterocyclic ring (Formula (IV)), and an aromatic 6-membered heterocyclic pyridine ring (Formula (V)).

In Formula (II), $Z^1$ is N or P, each $X^1$ independently is F, CN, alkenyl, alkynyl, carbonate ester, fluoro-substituted alkyl, or cyano-substituted alkyl; n is 0 or an integer from 1 to 10; and $R^3$ and $R^4$ are as defined in Formula (I). In Formula (II) at least one of $X^1$, $R^3$, and $R^4$ bears at least one substituent comprising a fluoro, cyano, carbonate ester, alkenyl group (e.g., allyl or vinyl), or alkynyl group (e.g., propargyl).

In Formula (III), $Z^1$ is N or P, each $X^2$ independently is F, CN, alkenyl, alkynyl, carbonate ester, fluoro-substituted alkyl, or cyano-substituted alkyl; n is 0 or an integer from 1 to 8; and $R^1$ and $R^2$ are as defined in Formula (I). In Formula (II) at least one of $X^2$, $R^3$, and $R^4$ bears at least one substituent comprising a fluoro, cyano, carbonate ester, alkenyl group (e.g., allyl or vinyl), or alkynyl group (e.g., propargyl).

In Formula (IV), $Z^2$ is N; $Z^3$ is N, O, or S; each of $X^3$, $X^4$, and $X^5$ independently is H, alkyl, F, CN, alkenyl, alkynyl, carbonate ester, fluoro-substituted alkyl, or cyano-substituted alkyl; and $R^3$ is as defined in Formula (I). In Formula (II) at least one of $X^3$, $X^4$, $X^5$, and $R^3$ bears at least one substituent comprising a fluoro, cyano, carbonate ester, alkenyl group (e.g., allyl or vinyl), or alkynyl group (e.g., propargyl).

In Formula (V), $Z^2$ is N; each of $X^6$, $X^7$, $X^8$, $X^9$, and $X^{10}$ independently is H, alkyl, F, CN, alkenyl, alkynyl, carbonate ester, fluoro-substituted alkyl, or cyano-substituted alkyl; and $R^3$ is as defined in Formula (I). In Formula (II) at least one of $X^6$, $X^7$, $X^8$, $X^9$, $X^{10}$, and $R^3$ bears at least one substituent comprising a fluoro, cyano, carbonate ester, alkenyl group (e.g., allyl or vinyl), or alkynyl group (e.g., propargyl).

The anion of the ionic liquid can be can be any anion that will provide an ionic liquid salt, such as, e.g., fluoroborate anion such as tetrafluoroborate ($BF_4^-$), pentafluoroethyl-trifluoroborate ($CF_3CH_2BF_3^-$), and the like; fluorinated bissulfonamides such as $N(SO_2F)_2^-$ (FSI), $N(SO_2CF_3)_2^-$ (TFSI), and the like; fluorinated diazolide anions such as 1-trifluoromethyl-3-cyano-4-cyano imidazolide anion (TDI), 3,5-trifluoromethyl-1,2-diazolide anion (TFPI), and the like.

Electrolytes comprising the ionic liquids of Formula (I) can include any lithium salt that is suitable for use as a lithium ion source in electrolytes for lithium-ion batteries, which salts are well known in the secondary battery art. Non-limiting examples of lithium salts useful in the electrolyte compositions described herein include, e.g., lithium bis(trifluoromethanesulfonyl)imidate (LiTFSI), lithium 2-trifluoromethyl-4,5-dicyanoimidazolate (LiTDI), lithium 4,5-dicyano-1,2,3-triazolate (LiTDI), lithium trifluoromethanesulfonate (LiTf), lithium perchlorate ($LiClO_4$), lithium bis(oxalato)borate (LiBOB), lithium difluoro(oxalato)borate (LiDFOB), lithium tetrafluoroborate ($LiBF_4$), lithium hexafluorophosphate ($LiPF_6$), lithium thiocyanate (LiSCN), lithium bis(fluorosulfonyl)imidate (LiFSI), lithium bis(pentafluoroethylsulfonyl)imidate (LBETI), lithium tetracyanoborate ($LiB(CN)_4$), lithium nitrate, combinations of two or more thereof, and the like. In some preferred embodiment, the lithium salt comprises lithium nitrate in combination with at least one other salt, e.g., LiTFSI. In a preferred embodiment, the lithium salt is LiFSI. The lithium salt can be present in the electrolyte at any concentration suitable for lithium-ion battery applications, which concentrations are well known in the secondary battery art. In some embodiments, the lithium salt is present in the electrolyte at a concentration in the range of about 0.1 M to about 10 M, about 1 M to about 6 M, about 1 M to about 5 M, or about 1 M to about 4 M.

The electrolyte compositions described herein also can optionally comprise an additive such as those described in Jow et al. (Eds.), *Electrolytes for Lithium and Lithium-ion Batteries*; Chapter 3, pp. 167-182; Springer; New York, NY (2014), which is incorporated herein by reference in its entirety. Such additives can provide, e.g., benefits such as SEI, cathode protection, Li salt stabilization, thermal stability, safety enhancement, overpotential protection, corrosion inhibition, and the like. The additive can be present in the electrolyte at any concentration, but in some embodiments is present at a concentration in the range of about 0.0001 M to about 0.5 M.

The electrolytes can be incorporated in a lithium-ion electrochemical cell comprising a positive electrode (cathode), a negative electrode (anode), and a porous separator between the cathode and anode, with the electrolyte in contact with both the anode and cathode, as is well known in the battery art. A battery can be formed by electrically connecting two or more such electrochemical cells in series, parallel, or a combination of series and parallel. The electrolyte can be utilized with any anode or cathode compositions useful in lithium-ion batteries.

Electrochemical cell and battery designs and configurations, anode and cathode materials, as well as electrolyte salts, solvents and other battery or electrode components (e.g., separator membranes, current collectors), which can be used in the electrolytes, cells and batteries described herein, are well known in the lithium battery art, e.g., as described in "Lithium Batteries Science and Technology" Gholam-Abbas Nazri and Gianfranco Pistoia, Eds., Springer Science+Business Media, LLC; New York, NY (2009) (also referred to herein as Nazri-2009), which is incorporated herein by reference in its entirety.

The separator component of the lithium-ion cell can be any separator used in the lithium battery art. A typical material is a porous polyalkylene material such as microporous polypropylene, microporous polyethylene, a microporous propylene-ethylene copolymer, or a combination thereof, e.g., a separator with layers of different polyalkylenes; a poly(vinylidene-difluoride)-polyacrylonitrile graft copolymer microporous separator; and the like. Examples of suitable separators are described in Arora et al., Chem. Rev. 2004, 104, 4419-4462, which is incorporated herein by reference in its entirety.

Processes used for manufacturing lithium cells and batteries are well known in the art. The active electrode materials are coated on both sides of metal foil current collectors (typically copper for the anode and aluminum for the cathode) with suitable binders such as polyvinylidene difluoride, or more preferably, a material such as carboxymethylcellulose (CMC), polyacrylic acid (PAA), or lithiated PAA (LiPAA), and the like, to aid in adhering the active materials to the current collectors. LiPAA is a particularly preferred binder for the anodes described herein.

The anode active material comprises an element or material that can accept lithium during charging, such as carbon, silicon, and various metal oxides metal sulfides and the like, e.g., as described in Nazri-2009, referred to above.

The cathode active material typically is a lithium metal oxide material. In some embodiments, the cathode can comprise a layered lithium metal oxide cathode material such as $LiMO_2$ wherein M=Mn, Ni, Co or a combination thereof (e.g., layered, $LiCoO_2$, a layered lithium nickelmanganese-cobalt oxide, often referred to as "NMC", such as $Ni_{0.5}Mn_{0.3}Co_{0.2}O_2$ (also known as "NMC532"), and similar materials). In other embodiments, the cathode can comprise a spinel lithium metal oxide such as $Li_2M'_2O_4$ wherein M'=Mn, Ni, Co or a combination thereof; a structurally integrated 'layered-layered' (LL) lithium metal oxide such as $xLi_2MnO_3 \cdot (1-x)LiMn_yM_{1-y}O_2$ wherein 0<x<1, 0≤y≤1, M=Ni, Co, or Ni and Co; a structurally integrated 'layered-spinel' (LS) lithium metal oxide such as $xLi_2MnO_3 \cdot (1-x)Li_2Mn_yM_{2-y}O_4$ wherein 0≤x≤1, 0≤y≤2, M=Ni, Co, or Ni and Co; a structurally integrated 'layered-layered-spinel' (LLS) lithium metal oxide such as $z[xLi_2MnO_3 \cdot Li_2Mn_yM_{2-y}O_4] \cdot (1-z)Li_2M'_2O_4$ wherein 0<x<1, 0≤y≤1, 0<z<1, M=Ni, Co, or Ni and Co, and M'=Mn, Ni, Co or a combination thereof (e.g., 0.85 $[0.25Li_2MnO_3 \cdot (0.75)LiMn_{0.375}Ni_{0.375}Co_{0.25}O_2]$ $\cdot 0.15Li_2M'_2O_4$ wherein M'=a combination of Mn, Ni, and Co); or any other cathode active material used in lithium-ion batteries.

As used herein, a structurally-integrated composite metal oxide is a material that includes domains (e.g., locally ordered, nano-sized or micro-sized domains) indicative of different metal oxide compositions having different crystalline forms (e.g., layered or spinel forms) within a single particle of the composite metal oxide, in which the domains share substantially the same oxygen lattice and differ from each other by the elemental and spatial distribution of metal ions in the overall metal oxide structure. Structurally-integrated composite metal oxides are different from and generally have different properties than mere mixtures of two or more metal oxide components (for example, mere mixtures do not share a common oxygen lattice).

Cell assembly typically is carried out on automated equipment. The first stage in the assembly process is to sandwich a separator between the anode. The cells can be constructed in a stacked structure for use in prismatic cells, or a spiral wound structure for use in cylindrical cells. The electrodes are connected to terminals and the resulting sub-assembly is inserted into a casing, which is then sealed, leaving an opening for filling the electrolyte into the cell. Next, the cell is filled with the electrolyte and sealed under moisture-free conditions.

Once the cell assembly is completed the cell can be subjected to one of more controlled charge/discharge cycles to activate the electrode materials. This is known as formation cycling. The formation cycling process is well known in the battery art and involves initially charging with a low voltage (e.g., substantially lower that the full-cell voltage) and gradually building up the voltage.

In another aspect, an improved method for preparing bis(fluorosulfonyl)imidate (FSI) salts of the cations described herein is provided. The nitrogen and phosphorus cation cation-based ionic liquids typically are prepared from tertiary amines, nitrogen heteroaromatic compounds, or tertiary phosphines by reaction with an alkylating agent such as an alkyl halide. If a non-halogen counter anion, such as FSI, is required, the halide anion typically must be exchanged for non-halogen anion such as FSI, e.g., using lithium FSI, followed by removal of lithium halide. This process inevitably introduces halide contaminants into the ionic liquid, which can affect electrochemical performance, as well as physical properties, such as viscosity.

This new method comprises contacting a precursor selected from the group consisting of a tertiary amine, a tertiary phosphine, and an aromatic nitrogen heterocycle, with an alkyl bis(fluorosulfonyl)imidate in an aprotic solvent (e.g., acetonitrile, diethyl ether, and ethyl acetate) to alkylate the nitrogen or phosphorus of the precursor, and directly form a nitrogen or phosphorus cation with an FSI counter anion in a single step, without the need for halogen exchange. Preferably, the precursor, the alkyl group of the alkyl bis(fluorosulfonyl)imidate, or both, includes at least one fluoro, cyano, carbonate ester, alkenyl, or alkynyl substituent such that the alkylated product comprises a cation of Formula (I).

The following non-limiting examples illustrate various features of the electrolytes and materials described herein, as well as methods of synthesizing such compounds.

EXAMPLES

General Procedures $LiNi_{0.5}Mn_{0.3}Co_{0.2}O_2$ cathodes (90% NMC532 (Toda Kogyo Corp.), 5% C45 conductive carbon (from Timcal), and 5% polyvinylidene difluoride (PVdF, SOLVAY 5130) by weight) were fabricated by Cell Analysis, Modeling, and Prototyping (CAMP) Facility at Argonne National Laboratory. Active material loading was 10.26 mg/cm$^2$ for NMC532 cathode. The electrolytes were prepared in an argon-filled glovebox by mixing testing ionic liquid with LiFSI (Nippon ShokuBai Co., Ltd.). The water content was <20 ppm, measured by using a coulometric Karl-Fischer titrator (METTLER TOLEDO C30). The viscosity was measured by a VISCOLAB 4000 viscometer at room temperature.

Electrolyte conductivity (a) was calculated using the resistance data obtained by electrochemical impedance spectroscopy (EIS) using SOLARTRON ANALYTICAL 1400 Cell test station. The distance between the electrodes (1) was kept equal to 0.172 cm using a Teflon spacer ring with the inner area (A) of 0.502 cm$^2$. Cell impedance was measured the frequency range of 1 MHz to 0.1 Hz at the open circuit potential (OCV).

Galvanostatic charge-discharge cycling tests were conducted on MACCOR electrochemical analyzer with Al-coated 2032-coin cells. All cells were assembled using NMC532 as cathode and lithium metal foil as the anode with a cutoff voltage of 4.3-3.0 V and 4.7-3.0 V. The separator was a glass micro-fiber disc. The effective electrode areas were 1.54 cm$^2$ for the cathode and 1.77 cm$^2$ for the anode. The cells were formed using three C/20 formation cycles followed by 100 cycles at C/10. All electrochemical experiments were conducted at 30° C.

Post-cycling analysis. The cycled coin cells were disassembled in the argon-filled glovebox, and the electrodes were thoroughly rinsed with anhydrous dimethyl carbonate and dried in a vacuum oven. The morphologies and the elemental mapping of the cycled electrodes were examined with scanning electron microscopy (SEM) and energy-dispersive X-ray spectroscopy (EDX) using a JOEL JCM-6000-PLUS spectrometer. Transmission electron microscopy (TEM) analysis was conducted in JOEL JEM-2100F spectrometer. The XPS analysis was conducted in a PHI 5000 VERSAPROBE II system (Physical Electronics) with a base pressure of about $2 \times 10^{-9}$ Torr. The spectra were obtained using an Al Kα radiation (hv=1486.6 eV) beam (100 m, 25 W), with Ar$^+$ and electron beam sample neutralization, in Fixed Analyzer Transmission mode with a pass energy of 11.75 eV. Shirley background subtraction and fitting to multiple Gaussian peaks were performed on all spectra using the MULTIPACK software from Physical Electronics. The area under the XPS peaks (sum of Gaussian components) was adjusted using manufacturer-calibrated Relative Sensitivity Factors and normalized to obtain elemental concentrations. The same normalization factors were used to plot XPS signal intensities as concentration per unit energy (at. % eV$^{-1}$). Binding energy was calibrated by shifting every region to align the C 1s peak of C—C/C—H environments at 284.8 eV.

Example 1. Synthesis of Ionic Liquids

A. Synthesis of MeFSI

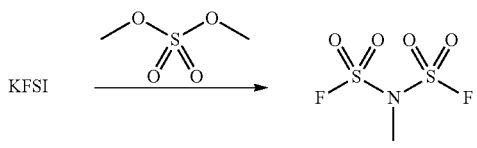

A 2 L round bottom flask was charged with potassium bis(fluorosulfonyl)imide (60 g, 276 mmol) and 1,4-dioxane (24 mL, 276 mmol), and dimethyl sulfate (400 mL, 4.2 mol) were added slowly. The mixture was heated to 100° C. for 3 h. After cooling back to 70° C., ice cold water (900 mL) was added into the flask slowly and the mixture was stirred at 70° C. for 1 h. After cooling back to room temperature, the mixture was extracted with CHCl$_3$ (200 mL×3). The combined organic layer was washed with H$_2$O (150 mL) and dried with Na$_2$SO$_4$. The volatiles were removed under vacuum to get the crude product. The final product was isolated by vacuum distillation to yield as colorless liquid (26.8 g, 50%, b.p. 70-75° C./50 torr). $^1$H NMR (300 MHz, Acetone-d$_6$) δ 3.85 (t, J=1.6 Hz, 3H). $^{19}$FNMR (282 MHz, Acetone-d$_6$) δ 53.83 (q, J=1.8 Hz).

B. Synthesis of PMpyr$_f$FSI

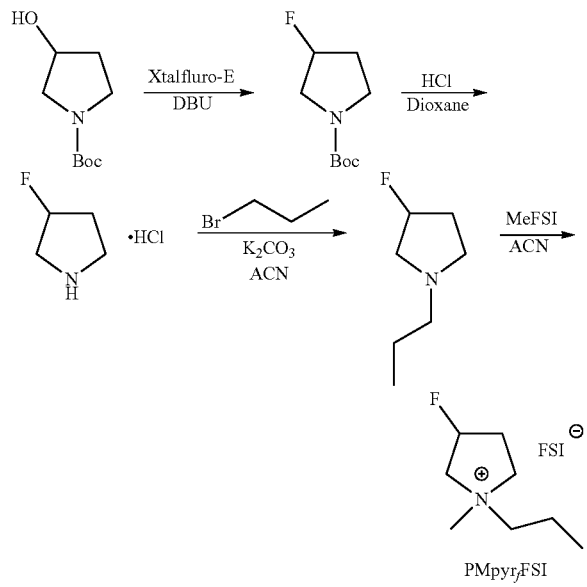

B(1). 1-Tert-butyloxycarbonyl-3-fluoropyrrolidine (1-Boc-3-fluoropyrrolidine)

A flask was charged with 1-boc-3-hydroxypyrrolidine (1.87 g, 10 mmol) and dichloromethane (DCM; 30 mL) and cooled to −78° C. (Diethylamino)difluorosulfonium tetrafluoroborate (XTALFLURO-E; 3.45 g, 15 mmol) and 1,8-Diazabicyclo[5.4.0]undec-7-ene (DBU; 2.25 mL, 15 mmol) were added at −78° C. and the mixture was stirred at −78° C. for 2 h and then the temperature was allowed to warm up to room temperature and stirred overnight. The reaction was quenched with NaHCO$_3$ (sat., 50 mL) and the aqueous layer was extracted with DCM (50 mL×3). The combined organic layer was washed by brine solution and dried with Na$_2$SO$_4$. The volatiles were removed under vacuum to yield a brown oil and the crude oil was purified by silica gel chromatography (5-10% ethyl acetate in hexanes) to give 0.9 g product (47.6%) as yellow oil. $^1$H NMR (300 MHz, CDCl$_3$) δ 5.21 (dt, J=52.9, 3.7 Hz, 1H), 3.59 (ddd, J=51.5, 26.4, 15.0 Hz, 4H), 2.35-2.11 (m, 1H), 1.95-1.85 (m, 1H), 1.47 (s, 9H). $^{19}$F{$^1$H} NMR (282 MHz, CDCl$_3$) δ −177.0, −177.4.

B(2). 3-Fluoropyrrolidine hydrochloride

A flask was charged with 1-Boc-3-fluoropyrrolidine (0.9 g, 4.7 mmol) and 1,4-dioxane (25 mL) and HCl solution (8 mL, 4 M in 1,4-dioxane) was added and the mixture was stirred at room temperature overnight in Ar-filled glovebox. The product was collected by filtration and rinsed with Et$_2$O as a light brown solid (0.36 g, 60%) and used in the next step without further purification. $^1$H NMR (300 MHz, D$_2$O) δ 5.48 (dt, J=51.7, 3.9 Hz, 1H), 3.88-3.11 (m, 4H), 2.69-1.68 (m, 2H). 1.47 (s, 9H). $^{19}$F{$^1$H} NMR (282 MHz, D$_2$O) δ −177.0.

B(3). 1-propyl-3-fluoropyrrolidine

A flask was charged with 3-fluoropyrrolidine hydrochloride (2.01 g, 16 mmol), K$_2$CO$_3$ (6.60 g, 48 mmol), 1-bromopropane (1.6 mL, 18 mmol) and acetonitrile (50 mL) and the mixture was heated to 50° C. and stirred for 2 days. The solid was filtered off and HCl solution (4 mL, 4 M in 1,4-dioxane) was added to the filtrate. The volatiles were removed under vacuum to yield a yellow solid and the solid was taken up into water (20 mL) and neutralized by NaOH (aq., 2.5 M). The aqueous layer was extracted with diethyl ether (Et$_2$O) (30 mL×3) and the combined organic layer was washed with brine solution. The majority of Et$_2$O was removed by distillation and the product was isolated by vacuum transfer as an Et$_2$O solution (5.0 g, with 3 eq. Et$_2$O and 0.1 eq. 1,4-dioxane per product, yield 88%) for the next step without further purification. $^1$H NMR (300 MHz, Acetone-d$_6$) δ 5.13 (dddt, J=56.2, 6.9, 5.1, 1.8 Hz, 1H), 2.81-2.46 (m, 3H), 2.40-2.10 (m, 4H), 1.98-1.71 (m, 1H), 1.70-1.37 (m, 2H), 0.89 (t, J=7.4 Hz, 3H), (1,4-dioxane is observed at δ3.58 as singlet and Et$_2$O is observed at δ3.40 and 1.11 as quartet and triplet, respectively). $^{19}$F{$^1$H}NMR (282 MHz, Acetone-d$_6$) δ-168.3.

B(4). 1-methyl-1-propyl-3-fluoropyrrolidinium bis(fluorosulfonyl)imide (PMpyr$_f$FSI)

To the Et$_2$O solution of 1-propyl-3-fluoropyrrolidine (5.0 g, with 3 eq. Et$_2$O and 0.1 eq. 1,4-dioxane per 1-propyl-3-fluoropyrrolidine), MeFSI (2.75 g, 14 mmol) was added slowly and the mixture was stirred at room temperature for 2 h. The volatiles were removed under vacuum to yield a light yellow oil. The crude was taken up in ethyl acetate (50 mL) and activate charcoal (4 g) was added and the mixture was stirred overnight. The activate charcoal was removed by filtration and the volatiles were removed under vacuum to yield colorless oil (3.9 g, 85%). The resulted IL was dried in lyophilizer for at least 2 days, then stored over 4 Å molecular sieves and filtered before use. $^1$H NMR (300 MHz, Acetone-d$_6$) δ 5.68 (d, J=54.6 Hz, 1H), 4.31-3.77 (m, 4H), 3.74-3.49 (m, 2H), 3.42 and 3.39 (s, 3H), 3.05-2.43 (m, 2H), 2.07-1.82 (m, 2H), 1.02 and 1.01 (t, J=7.2 Hz, 3H). $^{19}$F{$^1$H} NMR (282 MHz, Acetone-d$_6$) δ 51.4, −168.9, −172.4. $^{13}$C{$^1$H} NMR (75 MHz, Acetone-d$_6$) δ 92.79 (d, J=177.6 Hz), 71.47-69.82 (m), 68.34 (d, J=3.6 Hz), 64.68 (d, J=3.6 Hz), 51.08 (d, J=3.6 Hz), 31.52 (d, J=2.0 Hz), 17.87 (d, J=2.0 Hz), 10.82 (d, J=2.0 Hz).

C. Synthesis of PfMpyrFSI

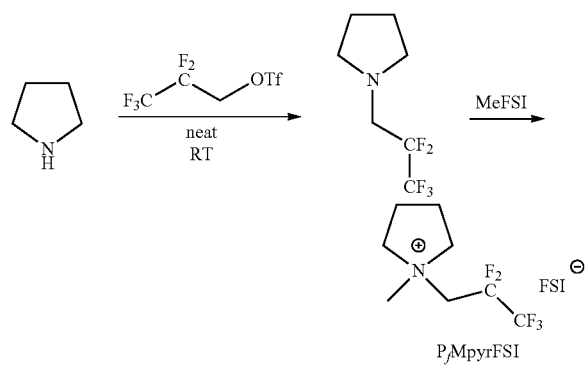

C(1). 1-(2,2,3,3, 3-pentafluoropropyl)pyrrolidine

A flask was charged with pyrrolidine (50 mL, 600 mmol) and cooled to 0° C. 2,2,3,3,3-pentafluoropropyl trifluoromethanesulfonate (33 mL, 200 mmol) was added at 0° C. and the temperature was allowed to warm up to room temperature and stirred overnight. The solids were removed by filtration and washed with Et$_2$O. The filtrate was diluted with Et$_2$O to a total volume of 120 mL and then the Et$_2$O layer was washed by 5% HCl (aq.) solution (120 mL×2). The Et$_2$O was removed by distillation and the product was isolated by distillation (36 g, 89%, b.p. 114-115° C.). $^1$H NMR (300 MHz, CDCl$_3$) δ 3.12 (t, J=15 Hz, 2H), 2.73 (br, 4H), 1.82 (br, 4H). $^{19}$FNMR (282 MHz, CDCl$_3$) δ −84.2, −119.6 (t, J=15.9 Hz).

C(2). 1-methyl-1-(2,2,3,3,3-pentafluoropropyl)pyrrolidinium bis(fluorosulfonyl)imide (PfMpyrFSI)

A flask was charged with 1-(2,2,3,3,3-pentafluoropropyl) pyrrolidine (20.3 g, 100 mmol) and ethyl acetate (200 mL), MeFSI (19.5 g, 14 mmol) was added slowly and the mixture was stirred at room temperature for 2 h. Then activated charcoal (20 g) was added and the mixture was stirred overnight. The activated charcoal was removed by filtration and the volatiles were removed under vacuum to yield colorless oil (33.2 g, 83%). The resulted IL was dried in lyophilizer for at least 2 days, then stored over 4 Å molecular sieves and filtered before use. $^1$H NMR (300 MHz, Acetone-d$_6$) δ 4.84 (t, J=16.7 Hz, 2H), 4.26-3.90 (m, 4H), 3.58 (s, 3H), 2.62-2.33 (m, 4H). $^{19}$F NMR (282 MHz, Acetone-d$_6$) δ 51.4, −85.75, −116.87 (t, J=16.7 Hz). $^{13}$C{$^1$H} NMR (75 MHz, Acetone-d$_6$) δ 120.6 (qt, J=382.0, 33.9 Hz), 115.6 (tq, J=389.2, 38.4 Hz), 68.7, 60.3 (t, J=17.9 Hz), 50.6, 22.0.

D. Synthesis of Additional Ionic Liquid Examples

1-Methyl-1-allylpyrrolidinium bis(fluorosulfonyl)imide and 1-methyl-1-(3-cyanopropyl)pyrrolidinium bis(fluorosulfonyl)imide were synthesized by the same general procedure as 1-methyl-1-(2,2,3,3,3-pentafluoropropyl)pyrrolidinium bis(fluorosulfonyl)imide.

E. Synthesis of Comparative Ionic Liquids (1-methyl-1-propylpiperidinium FSI, and 1-methyl-1-propyl pyrrolidinium FSI)

The comparative ionic liquids were obtained by the ion exchange reaction of the 1-methyl-1-propylpiperidinium bromide (from IoLiTec Inc.) or 1-methyl-1-propyl pyrrolidinium bromide with LiFSI (from Nippon ShokuBai Co., Ltd.). The resulting ionic liquids were extracted with ethyl acetate, and washed with de-ionized water until no residual halides were detected with use of saturated (sat.) AgNO$_3$. The products were dried in lyophilizer for at least 2 days, then stored over 4 Å molecular sieves and filtered before use.

The water content was less than 30 ppm, which were measured by using METTLER TOLEDO C30 coulometric Karl-Fischer titrator. The viscosity was measured by VIS-COLAB 4000 viscometer at room temperature.

F. Results and Discussion

Table 1 provides viscosity measurements for the ionic liquids described herein in comparison to 1-methyl-1-propylpiperidinium FSI, and 1-methyl-1-propyl pyrrolidinium FSI.

Scheme 1 compares (a) a traditional two step synthesis of FSI-based ionic liquids with (b) the one-step synthesis as described herein.

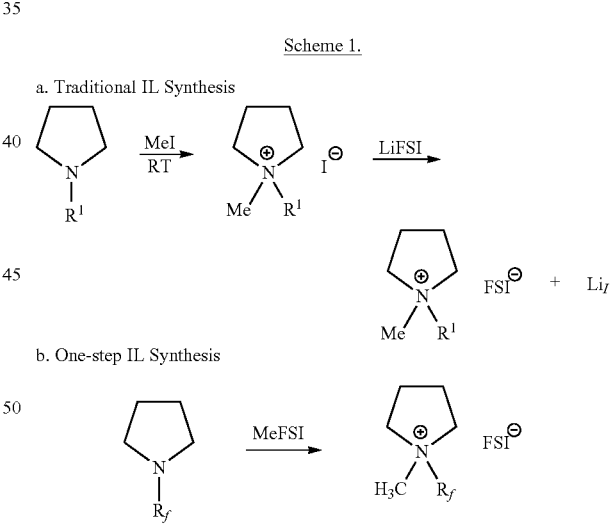

TABLE 1

| Compound | Viscosity/η (cP) |
|---|---|
| (structure) | 82.85 |

TABLE 1-continued

| Compound | Viscosity/$\eta$ (cP) |
|---|---|
| Pyrrolidinium with N-CH$_2$-CF$_2$-CF$_3$ substituent, FO$_2$S-N$^\ominus$-SO$_2$F | 261.2 |
| Pyrrolidinium with N-allyl substituent, FO$_2$S-N$^\ominus$-SO$_2$F | 37.08 |
| Pyrrolidinium with N-propyl-CN substituent, FO$_2$S-N$^\ominus$-SO$_2$F | 304.5 |
| Pyrrolidinium with N-butyl substituent, FO$_2$S-N$^\ominus$-SO$_2$F | 39.2 |
| Piperidinium with N-methyl, N-butyl, FO$_2$S-N$^\ominus$-SO$_2$F | 85.66 |

Discussion. The traditional method of ionic liquid synthesis includes two steps as shown in Scheme 1, line (a). First, quaternization of a tertiary amine (e.g., where R$^1$=alkyl) with alkyl halide (e.g., methyl iodide) to form quaternary ammonium salt, and second, anion metathesis of the quaternary ammonium salt with Li salt that contains target anion (e.g., FSI$^-$) to form the target ionic liquid. For Li-ion battery applications, solvent purity is critical for good cycling performance. The traditional ionic liquid synthesis method introduces potential halide contaminations through the alkyl halide. Purification of the contaminated ionic liquid requires extensively aqueous washing and determination of complete removal of halide impurities is based on no precipitation formation from a AgNO$_3$ test of aqueous wash, which is an arbitrary method for high purity electrolyte solvent preparation. Moreover, the availability and purity of the Li salt in the second synthesis step determines the accessibility and purity of the final ionic liquid.

In contrast, the methods described herein (e.g., as in Scheme 1 line (b), where Rf is a fluorinated alkyl) involve only one step from the tertiary amine, i.e., functionalized pyrrolidines are treated with MeFSI to form the target ionic liquid directly. Eliminating the usage of alkyl halide, also eliminates halide contamination. Furthermore, both functionalized pyrrolidines and MeFSI can be purified by distillation to avoid any non-volatile impurities in the final product.

Example 2. Electrochemical Evaluation of Ionic Liquids

Figure 2:
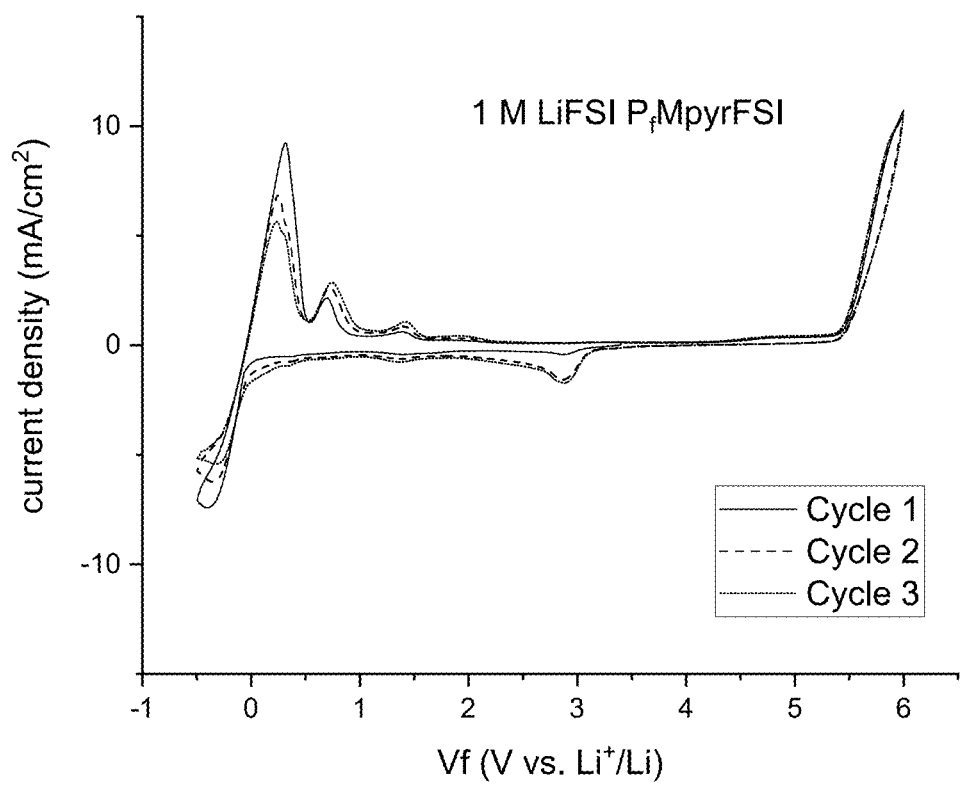
FIG. 2 shows a cyclic voltammetry plot of PM$_f$pyrFSI with 1 M LiFSI.

Cyclic voltammetry of the PMpyr$_f$FSI and PMppyrFSI with 1 M LiFSI are shown in FIG. 1 (PMpyr$_f$FSI) and FIG. 2 (PfMpyrFSI). Both ionic liquids show a wide electrochemical window and high voltage stability up to 5.5 V, which is slightly improved from the non-functionalized PMpyrFSI (5.4 V). Table 1 summarized the viscosity and conductivity of the PMpyrFSI, PMpyr$_f$FSI and PM$_f$pyrFSI at 25° C. After introducing fluoride into the cations, the viscosity of PMpyr$_f$FSI and PMppyrFSI increase to 83 and 261 cP, respectively, from the 40 cP of PMpyrFSI. Correspondingly, the conductivity for PMpyr$_f$FSI and PMfpyrFSI decrease.

Figure 3:
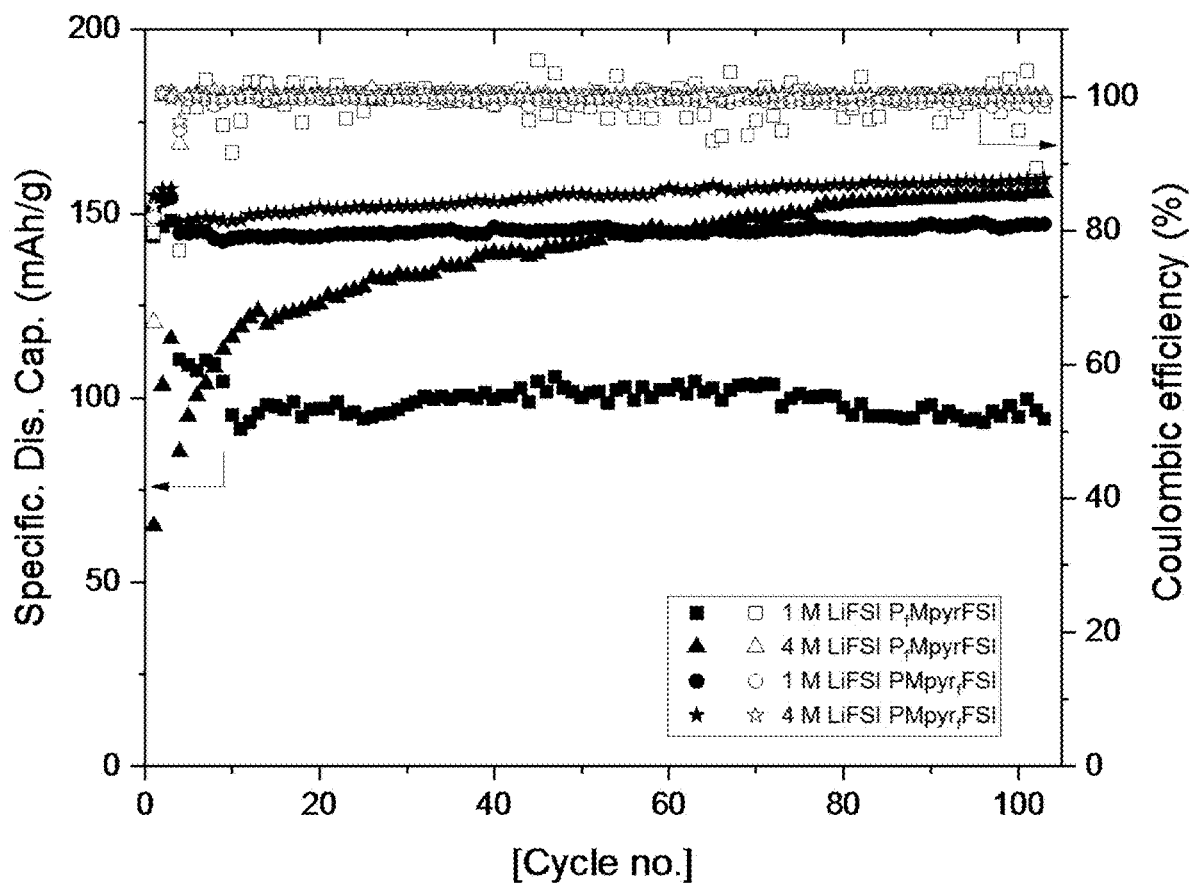
FIG. 3 illustrates the cycling performance of PMpyr$_f$FSI and PM$_f$pyrFSI in NMC532/Li cells cycled from 3.0-4.3 V.

FIG. 3 shows the cycling performance of 1 M LiFSI-PMpyr$_f$FSI electrolyte and 1 M LiFSI-PM$_f$pyrFSI electrolyte in a NMC532/Li cell with a cutoff voltage of 4.3-3.0 V. A 145 mAh/g initial specific discharge capacity and a 147 mAh/g specific discharge capacity at cycle 100 were obtained for 1 M LiFSI-PMpyr$_f$FSI electrolyte. Possible reasons for the slightly increased capacity are two-fold: (1) PMpyr$_f$FSI has high electrochemical stability resulting in nearly no capacity fading in the first 100 cycles, and (2) the intrinsic high viscosity of the ionic liquid causes a slow wetting process. However, for 1 M LiFSI-PMfpyrFSI electrolyte, the viscosity of this ionic liquid is three times higher than the 1 M LiFSI-PMpyr$_f$FSI electrolyte, and the initial specific discharge capacity is only around 115 mAh/g for LiFSI-PM$_f$pyrFSI. These two ionic liquids were also with increased LiFSI salt concentration. The super-concentrated ILs described herein show improved cyclability and rate capability compared to dilute systems described in previous studies. For 4 M LiFSI-PMpyr$_f$FSI, the initial specific discharge capacity slightly increased to 148 mAh/g, and slow wetting was observed for this electrolyte as the specific discharge capacity, which slowly increased during cycling and reached 159 mAh/g at cycle 100. For 4 M LiFSI-P$_f$MpyrFSI, similarly, due to the high solvent viscosity, the initial specific discharge capacity is only 85 mAh/g. The slow wetting was also observed for this electrolyte, and specific discharge capacity increase during cycling, reaching 156 mAh/g at cycle 100, which is dramatically improved from the 1 M LiFSI-PfMpyrFSI results.

Figure 4:
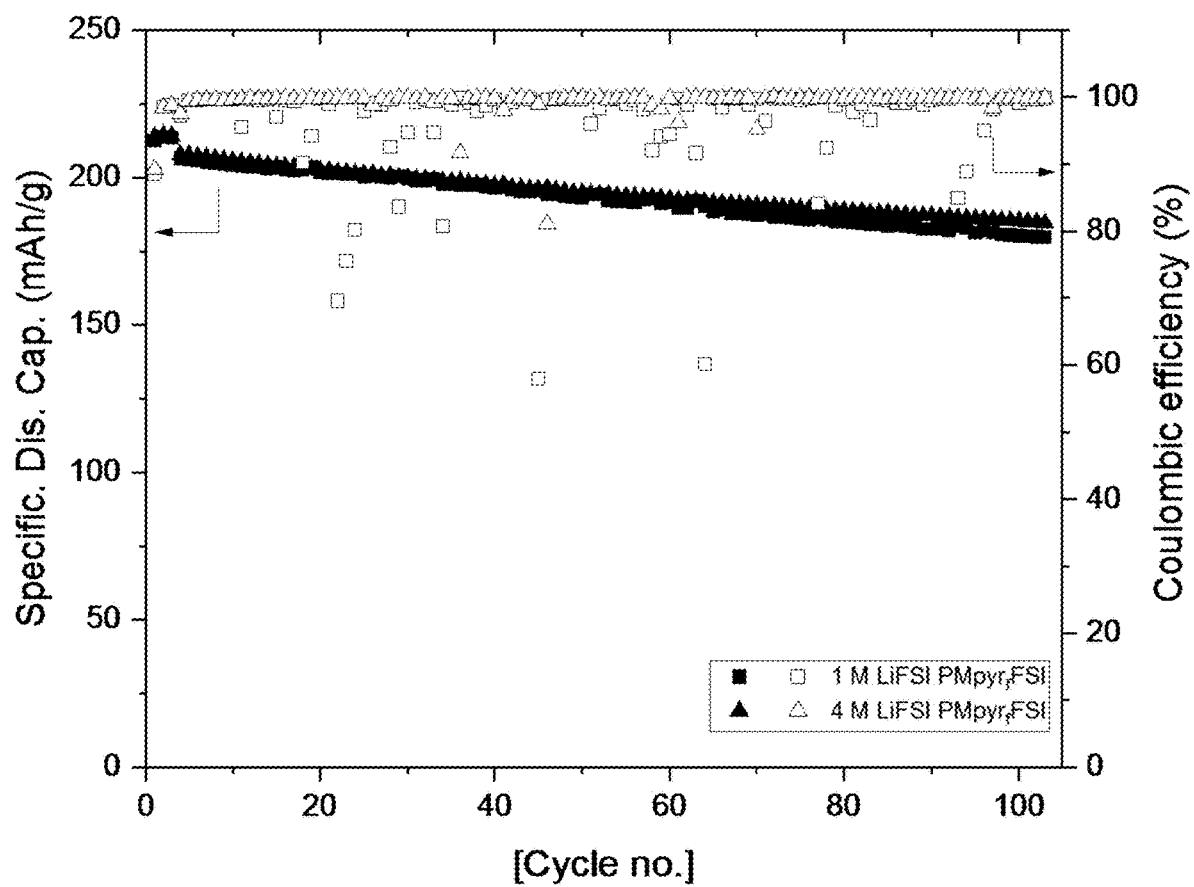
FIG. 4 illustrates cycling performance of PMpyr$_f$FSI in NMC532/Li cells cycled from 3.0-4.7 V.

Encouraged by the good cycling performance of 1 M LiFSI-PMpyr$_f$FSI and 4 M LiFSI-PMpyr$_f$FSI electrolyte at 4.3 V, this ionic liquid was then evaluated under high voltage conditions with 4.7 V upper cutoff voltage in a NMC532/Li cell. Initial specific discharge capacity was 206 mAh/g for 1 M LiFSI-PMpyr$_f$FSI, and the capacity retention at cycle 100 was 87%. With increased salt concertation (4 M LiFSI-PMpyr$_f$FSI), the initial specific discharge capacity was 207 mAh/g and the capacity retention increased to 89% at cycle 100 (FIG. 4).

Example 3. Electrochemical Cells

Figure 5:
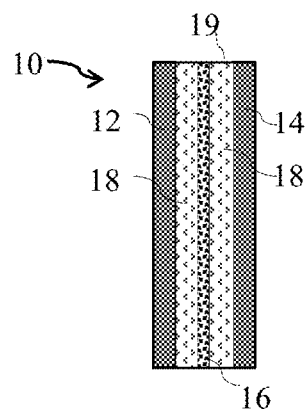
FIG. 5 schematically illustrates a lithium-ion electrochemical cell.
Figure 6:
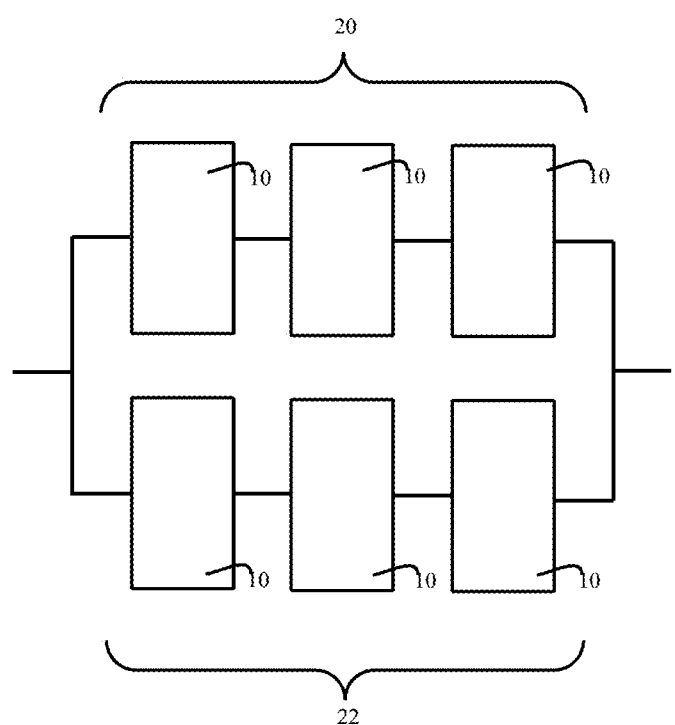
FIG. 6 schematically illustrates a lithium-ion battery.

FIG. 5 schematically illustrates a cross-sectional view of lithium-ion electrochemical cell 10 comprising cathode 12, and anode 14, with porous separator membrane 16 therebetween. Electrolyte 18, comprising a solution of a lithium salt in an ionic liquid described herein, contacts electrodes 12 and 14 and separator 16. The electrodes, separator and electrolyte are sealed within housing 19. FIG. 6 schematically illustrates a lithium-ion battery comprising a first array 20 consisting of three series-connected electrochemical cells 10, and a second array 22 consisting of three series-connected electrochemical cells 10, in which first array 20 is electrically connected to second array 22 in parallel.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Embodiments of the invention in which an exclusive property or privilege is claimed are defined as follows:

1. A method of preparing an ionic liquid comprising a nitrogen cation and a bis(fluorosulfonyl)imidate (FSI) counter anion; the method comprising contacting a precursor selected from the group consisting of a tertiary amine and an aromatic nitrogen heterocycle, with an alkyl bis(fluorosulfonyl)imidate in an aprotic solvent, at a temperature of about 20 to 25° C. until the nitrogen of the precursor is alkylated, thereby directly forming a nitrogen cation with an FSI counter anion.

2. The method of claim 1, wherein the aprotic solvent is selected from the group consisting of acetonitrile, diethyl ether, and ethyl acetate.

3. The method of claim 1, wherein the aprotic solvent is acetonitrile.

4. The method of claim 1, wherein the alkyl of the alkyl bis(fluorosulfonyl)imidate is a $C_1$ to $C_6$ alkyl group.

5. The method of claim 1, wherein the alkyl bis(fluorosulfonyl)imidate is methyl bis(fluorosulfonyl)imidate.

6. The method of claim 1, wherein one or more carbon of the tertiary amine or the aromatic nitrogen heterocycle bears at least one substituent selected from the group consisting of fluoro, cyano, alkenyl, alkynyl, a carbonate ester, fluoro-substituted alkyl, or cyano-substituted alkyl.

7. The method of claim 1, wherein the precursor is a tertiary amine.

8. The method of claim 7, wherein the tertiary amine comprises an N-alkyl-substituted 5 membered ring non-aromatic nitrogen heterocycle.

9. The method of claim 1, wherein the cation is a cation of Formula (I):

wherein:
$Z^1$ is N;
x is 1;
each of $R^1$ and $R^2$ independently comprises a hydrocarbyl group; or $R^1$ and $R^2$ together with $Z^1$ constitute a non-aromatic 5-membered heterocyclic ring;
$R^3$ is the alkyl from the alkyl bis(fluorosulfonyl)imidate;
$R^4$ is a hydrocarbyl group; and
one or more of $R^3$, $R^4$, and the non-aromatic 5-membered heterocyclic ring bears at least one substituent selected from the group consisting of fluoro, cyano, a carbonate ester, alkenyl group, or alkynyl.

10. The method of claim 9, wherein one or more of $R^3$, $R^4$, and the non-aromatic 5-membered heterocyclic ring bears at least one fluoro substituent.

11. The method of claim 1, wherein the precursor is an aromatic nitrogen heterocycle.

12. The method of claim 11, wherein the aromatic nitrogen heterocycle is selected from the group consisting of an aromatic 5-membered heterocycle and an aromatic 6-membered heterocycle.

13. The method of claim 12, wherein the aromatic 5-membered heterocycle is selected from the group consisting of a 1,3-thiazole, and a 1,3-oxazole; and the aromatic 6-membered heterocycle is selected from the group consisting of a pyridine, a 1,4-pyrazine, a 1,3-pyrazine, a 1,3,5-triazine, a 1,2,4-triazine, and a 1,2,3-triazine.

14. The method of claim 11, wherein the cation is a cation of Formula (I):

wherein:
$Z^1$ is N;
x is 0;
$R^1$ and $R^2$ together with $Z^1$ constitute an aromatic nitrogen heterocyclic ring;
$R^3$ is the alkyl from the alkyl bis(fluorosulfonyl)imidate; and
one or more of $R^3$ and the aromatic nitrogen heterocyclic ring bears at least one substituent comprising a fluoro, cyano, a carbonate ester, alkenyl group, or alkynyl group.

15. The method of claim 14, wherein one or more of $R^3$ and the aromatic nitrogen heterocyclic ring bears at least one fluoro group.

16. The method of claim 14, wherein the aromatic nitrogen heterocyclic ring is a pyridine.

17. The method of claim 14, wherein the aromatic 5-membered heterocyclic ring is selected from the group consisting of a 1,3-thiazole, and a 1,3-oxazole; and the aromatic 6-membered heterocycle is selected from the group consisting of a pyridine, a 1,4-pyrazine, a 1,3-pyrazine, a 1,3,5-triazine, a 1,2,4-triazine, and a 1,2,3-triazine.

18. A method of preparing an ionic liquid comprising a cation of Formula (V), wherein $Z^2$ is N,

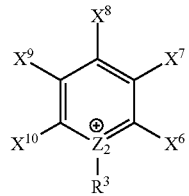

(V)

and a bis(fluorosulfonyl)imidate (FSI) counter anion;
the method comprising contacting a pyridine precursor of the cation, with an alkyl bis(fluorosulfonyl)imidate in an aprotic solvent to alkylate the nitrogen of the pyridine and thereby form the cation of Formula (V) and the FSI counter anion;

wherein:
$X^6$, $X^7$, $X^8$, $X^9$, and $X^{10}$ independently are H, alkyl, F, CN, alkenyl, fluoro-substituted alkyl, or cyano-substituted alkyl;
$R^3$ is the alkyl of the alkyl bis(fluorosulfonyl)imidate; and
one or more of $R^3$, $R^4$, $X^1$, $X^2$, $X^3$, $X^4$, $X^5$, $X^6$, $X^7$, $X^8$, $X^9$, and $X^{10}$ bears at least one substituent comprising a fluoro, cyano, carbonate ester, alkenyl group, or alkynyl group.

19. The method of claim 18, wherein the pyridine precursor of the cation and the alkyl bis(fluorosulfonyl)imidate are contacted at a temperature of about 20 to 25° C. until the nitrogen of the pyridine precursor is alkylated.

* * * * *